United States Patent [19]

Takaishi et al.

[11] 3,976,710

[45] Aug. 24, 1976

[54] PROCESS FOR THE PREPARATION OF TRICYCLO[5.3.1.0$^{3,8}$]UNDECANE

[75] Inventors: Naotake Takaishi, Iwademachi; Yoshiaki Inamoto, Wakayama; Kiyoshi Tsuchihashi, Kainan, all of Japan

[73] Assignee: Kao Soap Co., Ltd., Tokyo, Japan

[22] Filed: May 30, 1975

[21] Appl. No.: 582,166

[30] Foreign Application Priority Data

May 31, 1974 Japan................................. 49-62232

[52] U.S. Cl..................... 260/666 PY; 260/666 M; 260/617 R
[51] Int. Cl.$^2$.......................................... C07C 13/54
[58] Field of Search.................. 260/666 PY, 666 M

[56] References Cited
OTHER PUBLICATIONS

Krantz et al., Chem. Commun. 1971, 1287.

Krantz et al., J. Amer. Chem. Soc., 95, 5662, 1973.

Schleyer et al., Chem. Letters, 1189, 1973.

N. S. Vorobeva, O. A. Arefev, V. I. Epshev and A. A. Petrov, Chem. Ab., 75: 19562e, Neftekhimiya, 11, 163, 1971.

Naotake Takaishi et al., J. Org. Chem., 40, No. 3, pp. 276–281, 1975.

*Primary Examiner*—Veronica O'Keefe
*Attorney, Agent, or Firm*—Woodhams, Blanchard and Flynn

[57] ABSTRACT

A process for the preparation of tricyclo[5.3.1.0$^{3,8}$]undecane which comprises isomerizing 5,6-exo-trimethylenenorbornyl-2-carbinol in the presence of an acid catalyst and a hydride donor.

5 Claims, No Drawings

PROCESS FOR THE PREPARATION OF TRICYCLO[5.3.1.0³,⁸]UNDECANE

BACKGROUND OF THE INVENTION

1. Field of the Invention

This invention relates to a process for synthesizing tricyclo[5.3.1.0³,⁸]undecane (hereinafter referred to as "4-homoisotwistane"). More particularly, this invention relates to a process for converting 5,6-exo-trimethylenenorbornyl-2-carbinol (I) to 4-homoisotwistane (II) at a high selectivity by isomerizing 5,6-exo-trimethylenenorbornyl-2-carbinol (I) in the presence of an acid catalyst and a hydride donor as shown by the following reaction scheme (1):

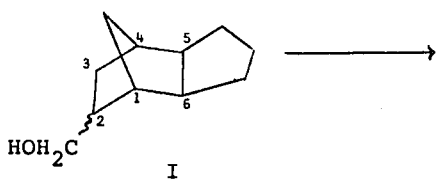

(1)

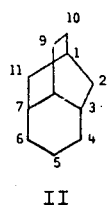

The symbol ~ indicates that the —CH₂OH moiety is in either endo or exo configuration.

2. Description of the Prior Art

4-Homoisotwistane (II) is a known useful compound having a tricyclic basket-like molecular structure analogous to that of adamantane. In addition to its known utility as an intermediate for preparing useful adamantane compounds, such as 1-methyladamantane, it and its derivatives are useful for pharmaceutical purposes, such as anti-viral agents, and they are also useful as additives for lubricating oils, fiber-treating oils, surface active agents and the like because of the inherent physical and chemical properties of polycyclic hydrocarbons. However, a process capable of effectively and easily preparing the basic substance of these valuable derivatives, namely 4-homoisotwistane (II), is not known.

4-Homoisotwistane (II) is a compound disclosed by Krantz et al (Chem., Commun., 1971, 1287 and J. Amer. Chem. Soc., 95, 5662 (1973)) in their report concerning the selectivity of the intermolecular Diels-Alder reaction of 1-penten-5-ylcyclohexadienes. However, the selectivity of 4-homoisotwistane (II) is very low in this reaction and the starting 1-penten-5-ylcyclohexadiene is not readily available or cannot easily be synthesized. Accordingly, from the industrial viewpoint, it is very disadvantageous to synthesize 4-homoisotwistane according to the process of Krantz et al. Majerski et al (Tetrahedron Letters, 4915 (1973)) succeeded in synthesizing 4-homoisotwistane (II) in a yield of about 20 percent by reacting homoadamant-4-ene or homoadamantan-4-ol with concentrated sulfuric acid and n-pentane. This process also is industrially disadvantageous because it is difficult to obtain the starting homoadamantane derivatives.

We previously found that when some tricycloundecanes, obtained by subjecting a suitable combination of butadiene, cyclopentadiene, cyclohexadiene, norbornene and the like to the Diels-Alder reaction and then hydrogenation, are isomerized under limited conditions, the reaction can be ended at the stage of 4-homoisotwistane (II) while preventing the reaction from further advancing to the stage of 1-methyladamantane and the compound (II) can be obtained in a high yield (Chemistry Letters, 1973, 1185).

SUMMARY OF THE INVENTION

This invention provides a process for synthesizing 4-homoisotwistane more easily and advantageously than the above-mentioned known processes.

The starting substance to be used in the process of this invention, namely, 5,6-exo-trimethylenenorbornyl-2-carbinol (I), is believed to be a novel compound. We synthesized this novel compound (I) in a high yield by reacting 2-exo-chloro-5,6-exo-trimethylenenorbornane (III) with metallic magnesium and treating the resulting Grignard reagent (IV) with formaldehyde as shown by the following reaction scheme (2):

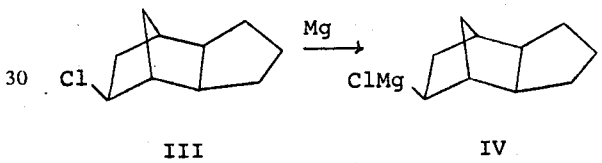

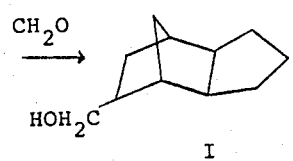

(2)

The 5,6-exo-trimethylenenorbornyl-2-carbinol (I) obtained according to this synthesis process is a mixture of two isomers in which the hydroxymethyl group is attached at the 2-position in exo- or endo-conformation. From the nmr spectrum, it was confirmed that the ratio of the two isomers present in the mixture is about 1 : 1.

The synthesis of the desired 4-homoisotwistane (II) from the starting substance (I) is accomplished by isomerizing the compound (I) in the presence of an acid catalyst and a hydride donor. We have not completely elucidated the mechanism according to which this reaction proceeds, but it is believed that, as shown in the following reaction scheme (3), 5,6-endo-trimethylenebicyclo[2.2.2]oct-2-yl cation (VII) is formed by the ring enlargement in the primary carbocation (carbonium ion) (V) formed by ionization of the carbinol (I) and the subsequent 1,2-alkyl-shift and the thus-formed cation is isomerized to the desired compound (II):

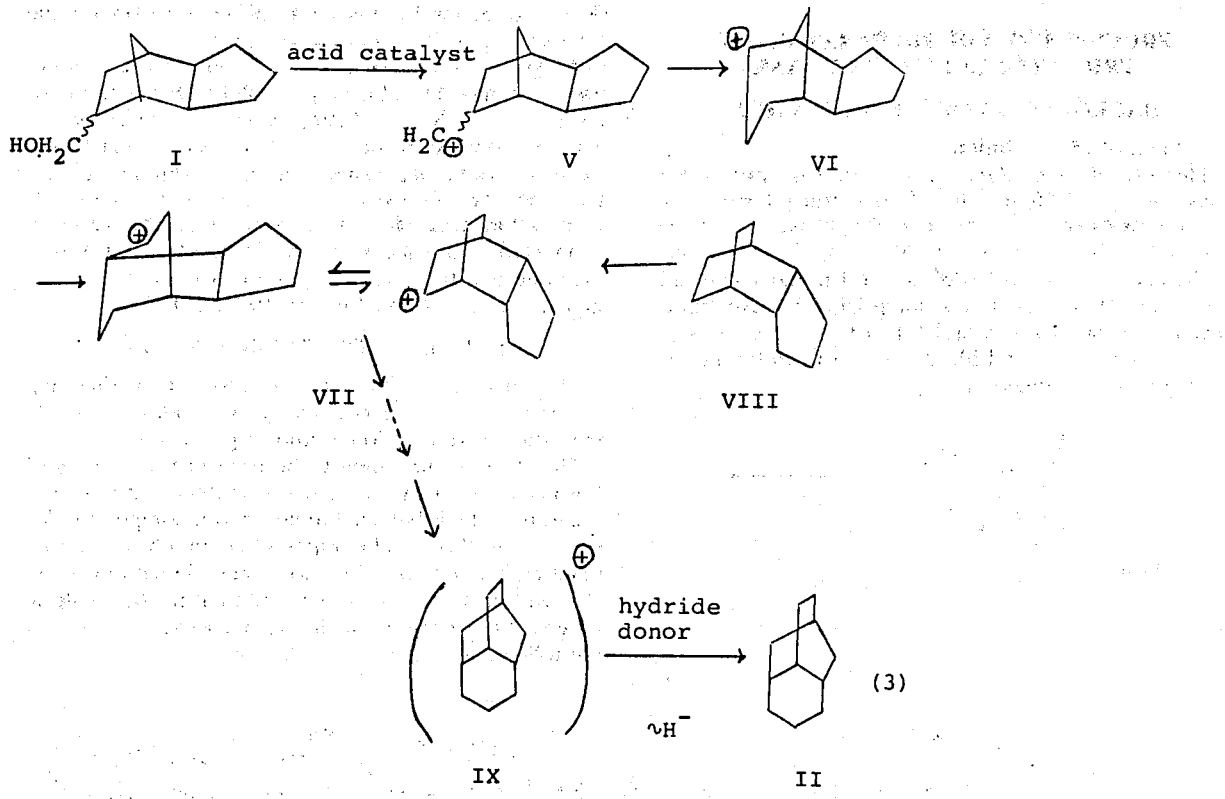

The isomerization reaction of 2,3-trimethylenebicyclo[2.2.2]octane (VIII) to 4-homoisotwistane (II) was previously described by us (Chemistry Letters, 1973, 1185).

The role of the acid catalyst in the process of this invention is deemed to be one of removing the hydroxy anion from the starting substance (I), whereby to form the carbocation (V). The thus-formed carbocation (V) will be successively isomerized by the mono-molecular reaction to the cation (IX) of the intended product (II). It is assumed that the hydride donor will furnish hydride to this cation (IX) and the intended product (II) will thus be formed.

As illustrated above, the unimolecular reaction in the process of this invention proceeds spontaneously. Accordingly, the process of this invention can be worked very easily, and the reaction advances smoothly by mixing the starting substance (I) with an acid catalyst and a hydride donor. In some cases, better results can be obtained when a reaction solvent is added, but it is generally preferred that an excess amount of hydride donor is used so that it acts also as the solvent. The starting substance (I) is soluble in most hydride donors (and solvents). If the catalyst is not homogeneously dissolved in the hydride donor (and solvents), it is necessary to agitate the reaction mixture sufficiently.

Any catalysts capable of ionizing the starting substance (II) to the carbocation can be used in this invention. For example, Bronsted acids represented by sulfuric acid, fluorosulfonic acid, chlorosulfonic acid, alkanesulfonic acid such as methanesulfonic acid, trifluoromethanesulfonic acid and ethanesulfonic acid and arenesulfonic acids such as benzenesulfonic acid and p-toluenesulfonic acid, and Lewis acids such as zinc chloride, aluminum halides, tin halides and antimony halides can be effectively used in the process of this invention. As the halides, it is preferred to use the chlorides and bromides. Of course, it is possible to use a suitable mixture comprising two or more of the foregoing catalysts. A catalytically effective amount of the catalyst is used, for example, from 0.01 to 100 moles, preferably from 0.1 to 10 moles of Brønsted acid, per 1 mole of I, and from 0.001 to 10 moles, preferably from 0.01 to 1 moles of Lewis acid, per 1 mole of I.

In this invention, any substances capable of supplying a basic hydrogen atom to the intermediate cation (IX) can be used as the hydride donor. From the industrial viewpoint, it is advantageous to use saturated hydrocarbons having 5 to 10 carbon atoms, for example, alkanes such as n-pentane, n-hexane, n-heptane, n-octane, i-hexane, i-heptane, i-octane, 2,2-dimethylbutane, 2,3-dimethylbutane, 2,5-dimethylhexane and 2,7-dimethyloctane, and cycloalkanes such as cyclopentane, cyclohexane, decalin, methylcyclohexane, dimethylcyclohexanes and trimethylcyclohexanes. The amount of hydride donor is not critical and it can be from 1 to 1000 moles, per 1 mole of I. An excess of hydride donor can be used to act as a solvent for the reaction. Other inert solvents can also be used.

The reaction proceeds at a temperature ranging from −80° to +100°C., but from the industrial viewpoint, it is preferred that the reaction be carried out at −10° to +60°C. At a temperature lower than −80°C., the reaction hardly occurs even if the strongest catalyst is employed. When the reaction is conducted at a temperature higher than +100°C., formation of undesired tar-like by-products increases.

This invention will now be described in more detail by reference to the following illustrative Example that by no means limits the scope of this invention. A synthesis of the starting substance (I) is described in the following Preparation.

Preparation

According to the process of Gilman et al (Org. Syntheses Coll., vol. 1, 188), 5,6-exo-trimethylenenorbornyl-2-carbinol (I) was synthesized.

A four-necked round-bottomed flask was charged with 250 ml of diethyl ether and 15 g (0.62 mole) of small pieces of magnesium, and 1.25 ml of ethyl bromide was added dropwise to initiate the reaction. Then, a solution of 85 g (0.5 mole) of 2-exo-chloro-5,6-exo-trimethylenenorbornane (III) synthesized according to the process of Youngblood et al (J. Org. Chem., 21, 1436 (1956)) in 100 ml of diethyl ether was added dropwise at such a rate that the ether was refluxed. After completion of the dropwise addition, the reaction mixture was heated and refluxed to prepare the Grignard reagent. Separately, 25 g of paraformaldehyde dried in a vacuum over a desiccator was heated at 180° to 200°C. in an oil bath to generate formaldehyde by depolymerization. The thus-formed formaldehyde was gradually introduced into the above solution of the Grignard reagent under a current of dry nitrogen.

After completion of the reaction, the reaction mixture was placed on 200 g of broken ice pieces and 30 percent $H_2SO_4$ was added thereto to dissolve therein the magnesium hydroxide formed by the reaction. Extraction with diethyl ether was conducted twice, followed by washing with an aqueous solution of sodium bicarbonate, drying with anhydrous sodium sulfate and fractionation.

A fraction boiling at 88° to 90°C. under 2 mm Hg was recovered to obtain 21.9 g (yield = 26%) of 5,6-exo-trimethylenenorbornyl-2-carbinol (I).

Elemental Analysis Values: Found: C = 78.4%, H = 10.6%. Calculated as $C_{11}H_{18}O$: C = 79.46%, H = 10.92%.

ir(cm$^{-1}$): 3310, 2920, 2845, 1475, 1450, 1027, 1009.

mass (m/e) (relative intensity, %): 166 (M$^+$, 3), 148 (M$^+$—H$_2$O, 42), 135 (M$^+$—H$_2$O—CH$_3$, 100), 120 (19), 119 (33), 107 (27), 95 (21), 94 (17), 93 (23), 91 (25), 80 (40), 79 (65), 67 (88).

nmr (ppm, CDCl$_3$ solvent), $\delta$ : 3.53 (doublet, 1H, —CH$_2$OH), 3.36 (doublet, 1H, -CH$_2$OH), 1.97 (singlet, 1H, OH), 2.4 – 0.8 (complex multiplet, 15H)

Two pairs of doublets having an intensity ratio of about 1 : 1 were observed at $\delta$ 3.53 and $\delta$ 3.36. Further, from the results of the elemental analysis and mass spectrum, the structure of 5,6-exo-trimethylenenorbornyl-2-carbinol (I) was confirmed. In view of the foregoing, it is construed that the product was a 1 : 1 mixture of exo- and endo-2-carbinols. They could not be separated from each other by customary gas chromatography (silicone SE-30, column temperature = 140°C.).

EXAMPLE 3.3g (0.02 mole) of 5,6-exo-trimethylenenorbornyl-2-carbinol (I) (mixed isomers) obtained in the Preparation was dissolved in 50 ml of n-pentane, and .15 ml of concentrated sulfuric acid was added to the solution under ice cooling and agitation. The temperature was gradually elevated to room temperature (20°–25°C.) and the reaction mixture was agitated overnight. The reaction mixture was placed in ice water under agitation, and diethyl ether extraction was conducted three times by using 100 ml of diethyl ether each time. The diethyl ether layers were washed with water, dried with anhydrous sodium sulfate and fractionated. A fraction boiling at 90° to 92°C. under 14 mm Hg was recovered to obtain 0.75 g (yield = 20%) of tricyclo[5.3.1.0$^{3,8}$]undecane (II).

Melting Point: 62° – 63°C. (sealed tube).

Elemental Analysis Values: Found: C = 87.6%, H = 12.4%. Calculated as $C_{11}H_{18}$: C = 87.92%, H = 12.08%.

ir(cm$^{-1}$): 2925, 2890, 2870, 2850, 1480, 1465, 1450, 1440, 1340, 975, 940, 895, 845.

ms (m/e) (relative intensity, %): 150 (M$^+$, 100), 122(39), 121 (39), 109 (12), 108 (16), 107 (19), 93 (27), 81 (27), 80 (46), 79 (40), 67 (35), 55 (18), 41 (40).

$^1$Hnmr (ppm, CDCl$_3$ solvent), $\delta$ : 1.0 – 2.0 (complex multiplet).

$^{13}$Cnmr (CDCl$_3$ solvent, 15.1 MHz, TMS at 0 ppm): 15.2, 24.8, 26.3, 27.1, 30.9, 31.9, 32.3, 33.1.

All of these properties were in agreement with those of an authentic sample of tricyclo[5.3.1.0$^{3,8}$]undecane synthesized according to our previously proposed process (Chem. Lett., 1973, 1185).

The embodiments of this invention in which an exclusive property or privilege is claimed are defined as follows:

1. A process for preparing tricyclo[5.3.1.0$^{3,8}$]undecane (I) which comprises isomerizing 5,6-exo-trimethylenenorbornyl-2-carbinol, at a temperature in the range of from −80° to +100°C., in the presence of an acid catalyst selected from the group consisting of (1) at least one Bronsted acid, and (2) at least one Lewis acid, and in the presence of at least one hydride donor, until a substantial quantity of I is formed, and recovering I from the reaction mixture.

2. The process according to claim 1 wherein the temperature of the isomerization reaction is in the range of −10° to +60°C.

3. The process according to claim 1 in which the acid catalyst is at least one Bronsted acid selected from the group consisting of sulfuric acid, fluorosulfonic acid, chlorosulfonic acid, methanesulfonic acid, trifluoromethanesulfonic acid, ethanesulfonic acid, benzenesulfonic acid and p-toluenesulfonic acid.

4. The process of claim 1 in which the acid catalyst is at least one Lewis acid selected from the group consisting of zinc chloride, aluminum halides, tin halides and antimony halides.

5. The process of claim 1 in which the hydride donor is a saturated hydrocarbon having from 5 to 10 carbon atoms.

* * * * *